United States Patent [19]
Aldous et al.

[11] Patent Number: 5,750,527
[45] Date of Patent: May 12, 1998

[54] THIADIAZOLES AND THEIR USE AS ANTIPICORNAVIRAL AGENTS

[75] Inventors: David J. Aldous, Glenmore; Thomas R. Bailey, Phoenixville; Guy Dominic Diana; Theodore J. Nitz, both of Pottstown, all of Pa.

[73] Assignee: Sanofi, Paris, France

[21] Appl. No.: 863,388

[22] Filed: May 27, 1997

Related U.S. Application Data

[62] Division of Ser. No. 706,108, Aug. 30, 1996, Pat. No. 5,650,419, which is a division of Ser. No. 477,040, Jun. 7, 1995, Pat. No. 5,567,719, which is a division of Ser. No. 242,529, May 13, 1994, Pat. No. 5,453,433.

[51] Int. Cl.$^6$ .................. A61K 31/495; A61K 31/50; A61K 31/505
[52] U.S. Cl. .................. 514/252; 544/238; 544/333; 544/405; 514/256
[58] Field of Search .................. 544/405, 333, 544/238; 514/252, 256

[56] References Cited

U.S. PATENT DOCUMENTS 5,112,823  5/1992  Leyendecker et al. .................. 514/252

*Primary Examiner*—Johann Richter
*Assistant Examiner*—Laura L. Stockton
*Attorney, Agent, or Firm*—Michael D. Alexander; Mary P. Bauman; Paul E. Dupont

[57] ABSTRACT

Described herein are compound of the formula:

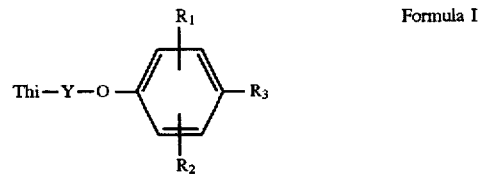

Formula I wherein:

Thi is thiadiazolyl or substituted thiadiazolyl;

Y is alkylene bridge of 3–9 carbon atoms;

$R_1$ and $R_2$ are each independently chosen from hydrogen, halo, alkyl, alkenyl, amino, alkylthio, hydroxy, hydroxyalkyl, alkoxyalkyl, alkylthioalkyl, alkylsulfinyl alkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl, or cyano;

$R_3$ is a heterocyclyl chosen from pyrimidinyl, pyrazinyl, or pyridazinyl;

or a pharmaceutically acceptable salt thereof which are effective antipicornaviral agents.

5 Claims, No Drawings

THIADIAZOLES AND THEIR USE AS ANTIPICORNAVIRAL AGENTS

CROSS-REFERENCE TO RELATED APPLICATIONS

This application is a division of application Ser. No. 08/706,108, filed Aug. 30, 1996, now U.S. Pat. No. 5,650,419, which is a division of application Ser. No. 08/477,040, filed on Jun. 7, 1995, now U.S. Pat. No. 5,567,719, which is a division of application Ser. No. 08/242,529, filed on May 13, 1994, now U.S. Pat. No. 5,453,433.

BACKGROUND OF THE INVENTION

1. Field of the Invention

This invention relates to novel heterocyclic substituted phenoxy alkyl thiadiazoles, to methods of preparation thereof, and to methods of use thereof as antipicornaviral agents.

2. Summary of the Invention

It has now been found that compounds of Formula I are effective antipicornaviral agents. Accordingly, the present invention relates to compounds of the formula;

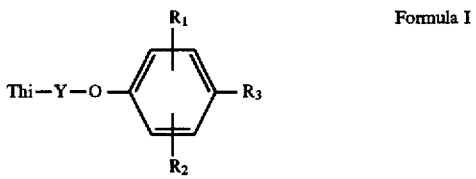

Formula I wherein:

Thi is thiadiazolyl or thiadiazolyl substituted with alkoxy, fluoromethyl, difluoromethyl, trifluoromethyl, 1,1-difluoroethyl, halo, alkyl, cycloalkyl, hydroxyalkyl, or alkoxyalkyl;

Y is an alkylene bridge of 3–9 carbon atoms;

$R_1$ and $R_2$ are each independently chosen from hydrogen, halo, alkyl, alkenyl, amino, alkylthio, hydroxy, hydroxyalkyl, alkoxyalkyl, alkylthioalkyl, alkylsulfinylalkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl, or cyano;

$R^3$ is alkoxycarbonyl, phenyl, alkyltetrazolyl, or heterocyclyl chosen from benzoxazolyl, benzothiazolyl, thiadiazolyl, imidazolyl, dihydroimidazolyl, oxazolyl, thiazolyl, oxadiazolyl, pyrazolyl, isoxazolyl, isothiazolyl, furyl, triazolyl, thienyl, pyridyl, pyrimidinyl, pyrazinyl, pyridazinyl, or substituted phenyl or substituted heterocyclyl wherein the substitution is with alkyl, alkoxyalkyl, cycloalkyl, haloalkyl, hydroxyalkyl, alkoxy, hydroxy, furyl, thienyl and fluoroalkyl; or a pharmaceutically acceptable acid addition salts thereof.

The invention also relates to compositions for combating picornaviruses comprising an antipicornavirally effective amount of a compound of Formula I with a suitable carrier or diluent, and to methods of combating picornaviruses therewith, including the systemic treatment of picornaviral infections in a mammalian host.

DETAILED DESCRIPTION OF PREFERRED EMBODIMENT

Compounds of Formula I are useful as antipicornaviral agents, and are further described hereinbelow.

Alkyl and alkoxy mean aliphatic radicals, including branched radicals, of from one to five carbon atoms. Thus the alkyl moiety of such radicals include, for example methyl, ethyl, propyl, isopropyl, n-butyl, sec-butyl, t-butyl, pentyl and the like.

Cycloalkyl means an alicyclic radical having from three to seven carbon atoms as illustrated by cyclopropyl, cyclobutyl, cyclopentyl, cycloheptyl, and cyclohexyl; and Halo means bromo, chloro, iodo, or fluoro.

Heterocyclyl or Het refers to a 5 or 6 membered carbon based heterocycle radical, having from one to about four nitrogen atoms and/or one oxygen or sulfur atom, provided that no two oxygen and/or sulfur atoms are adjacent in the heterocycle. Examples of these include furyl, oxazolyl, isoxazolyl, pyrazyl, imidazolyl, thiazolyl, tetrazolyl, thienyl, pyridyl, oxadiazolyl, thiadiazolyl, triazinyl, pyrimidinyl and the like. Heterocycle refers to the corresponding compounds.

The term heterocyclyl includes all known isomeric radicals of the described heterocycles unless otherwise specified, for example, thiadiazolyl encompasses 1,3,4-thiadiazol-2-yl, 1,2,4-thiadiazol-5-yl, and 1,2,4-thiadiazol-3-yl; thiazolyl encompasses 2-thiazolyl, 4-thiazolyl, and 5-thiazolyl and the other known variations of known heterocyclyl radicals. Thus any isomer of a named heterocycle radical is contemplated. These heterocycle radicals can be attached via any available nitrogen or carbon, for example, tetrazolyl contemplates 5-tetrazolyl or tetrazolyl attached via any available nitrogen of the tetrazolyl ring; furyl encompasses furyl attached via any available carbon, etc. The preparation of such isomers are well known and well within the scope of the skilled artisan in medicinal or organic chemistry.

Certain heterocycles can exist as tautomers, and the compounds as described, while not explicity describing each tautomeric form, are meant to embrace each and every tautomer. For example, pyridinone and its tautomer hydroxypyridine contemplate the same moiety. Inasmuch as the heterocyclic moieties of compounds of the present invention may be hydroxy-substituted, it is understood that such hydroxy-substituted heterocycles are intended to include the corresponding tautomers.

In the use of the terms hydroxyalkyl and alkoxyalkyl, it is understood that the hydroxy and alkoxy groups can occur at any available position of the alkyl. Thus hydroxyalkyl and alkoxyalkyl include, for example, hydroxymethyl, 1-hydroxyethyl, 2-hydroxyethyl, 2-hydroxypropyl, 2-hydroxyisopropyl, 2-, 3-, 4-, and 5-hydroxypentyl and the like; alkoxy refers to the corresponding alkyl ethers thereof.

In the use of the term hydroxyalkoxy, it is understood that the hydroxy group can occur at any available position of alkoxy other than the C-1 (geminal) position. Thus hydroxyalkoxy includes, for example, 2-hydroxyethoxy, 2-hydroxypropyoxy, 2-hydroxyisopropoxy, 5-hydroxypentoxy and the like.

Alkylene refers to a linear or branched divalent hydrocarbon radical of from 1 to about 5 carbon atoms such as methylene, 1,2-ethylene, 1,3-propylene, 1,4-butylene, 1,5-pentylene, 1,4-(2-methyl)butylene and the like. Alkylene can also contain alkenyl or alkynyl linkages.

Halogen refers to the common halogens fluorine, chlorine, bromine, and iodine.

As used herein, the term haloalkyl refers to a halo substituted alkyl, such as fluoroalkyl, chlorofluoroalkyl, bromochloroalkyl, bromofluoroalkyl, bromoalkyl, iodoalkyl, chloroalkyl, and the like where the haloalkyl has one or more than one of the same or different halogens substituted for a hydrogen. Examples of haloalkyl include ochlorodifluoromethyl, 1-chloroethyl, 2,2,2-trichloroethyl, 1,1-dichloroethyl, 2-chloro-1,1,1,2-tetrafluoroethyl, bromoethyl, and the like.

As used herein the term fluoroalkyl is a prefered subclass of haloalkyl, and refers to fluorinated and perfluorinated alkyl, for example fluoromethyl, difluoromethyl, trifluoromethyl, 2,2,2-trifluoroethyl, 1,2-difluoroethyl, 1,1, 2,3-tetrafluorobutyl, and the like.

The compounds of Formula I wherein R3 is a nitrogen-containing heterocycle are sufficiently basic to form acid addition salts and are useful both in the free base form and the form of acid-addition salts, and both forms are within the purview of the invention. The acid-addition salts are, in some cases, a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds can be prepared by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or by concentration of the solution or by any one of several other known methods. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance, and mass spectroscopy. The course of the reactions and the identity and homogeneity of the products were assessed by thin layer chromatography (TLC) or gas-liquid chromatography (GLC) or other art-accepted methods of monitoring organic chemistry reactions.

As described herein a noninteracting solvent can be N-methyl pyrrolidinone (NMP), methylene chloride ($CH_2Cl_2$), tetrahydrofuran (THF), benzene or any other solvent that will not take part in the reaction. In a preferred method, the preparation of compounds of the invention is done in dried solvents under an inert atmosphere. Certain reagents used in example preparations are specified by abbreviation, triphenylphosphine (TPP), triethylamine (TEA), diisopropylethylamine (DIPEA), and diethyl azodicarboxylate (DEAD). Ether is diethyl ether unless otherwise specified.

Compounds of Formula I can be prepared by several different methods.

Compounds of Formula I can be prepared by the reaction of the appropriate hydroxy-Y-thiadiazole and the appropriate $R_1$—$R_2$—$R_3$-phenol as described in U.S. Pat. No. 5,242, 924, incorporated herein by reference.

Compounds of Formula I can be prepared by reaction of the appropriate $R_1$—$R_2$—$R_3$-phenol and the appropriate halo-Y-thiadiazole by the reaction described in U.S. Pat. No. 4,942,241, incorporated herein by reference.

Compounds of formula I can also be prepared by elaborating the thiadiazolyl (Thi) moiety in the final steps of the synthesis:

For compounds of formula I where Thi is 1,2,4-thiadiazolyl; the X—Y—O—[$R_1$—$R_2$-4-$R_3$-phenyl] compound, where X is a functional group displaced by a suitably functionalized 1,2,4-thiadiazole. The X—Y—O—[$R_1$—$R_2$-4-$R_3$-phenyl] compounds are prepared from $R_1$—$R_2$-4-$R_3$ phenols and hydroxy —Y—X or halo—Y—X compounds, by the same methods used to prepare compounds of formula I described above. Typically X is in the w-position of Y (i.e., the furthest position in the alkylene bridge from phenoxy). Alternatively X can be placed on the Y—O[$R_1$—$R_2$-$R_3$-phenol] compound just prior to reaction with the functionalized thiadiazole. For example, where Y contains an w-alkene or alkyne the compound can be reacted with a suitable tin derivative, giving a compound wherein X is for example, tributyl. The tin—Y—O[$R_1$—$R_2$—$R_3$-phenyl] compound is then reacted with a halo-1,2,4-thiadiazole, preferably an iodo-1,2,4-thiadiazole to form a compound of formula I.

Alternatively the 1,2,4-thiadiazole can be elaborated from a functional group attached to Y, typically in the w position as described above. This method of preparing 1,2,4 thiadiazoles is well known in the art; see for example Katritzky and Rees *Comprehensive Heterocyclic Chemistry* (1985).

For compounds of formula I where Thi is 1,3,4 thiadiazole; the 1,3,4-thiadiazole is preferably elaborated from a functional group on Y in the final step. For example, the [alkoxycarbonyl]—Y—O—[$R_1$—$R_2$-4-$R_3$-phenyl] compound can be reacted to form a carbazide, then a activated sulfur compound, such as, Lawesson's reagent $P_4S_{10}$ or the like, which forms the 1,3,4-thiadiazole. Preparation of the X—Y—O—[$R_1$—$R_2$—$R_3$-phenyl] compound where X is a functional group is described above.

Alternatively the compound of formula I wherein Thi is 1,3,4-thiadiazole can be prepared by reacting a suitably functionalized 1,3,4-thiadiazole, with an X—Y—O—[$R_1$—$R_2$—$R_3$-phenyl] compound when X is a functional group displaced by 1,3,4-thiadiazole.

Compounds of formula I wherein $R_3$ is phenyl or heterocyclyl can be prepared by reacting a hydroxy-Y-thiadiazole or halo-Y-thiadiazole with a $R_1$—$R_2$-4-functionalized phenol, then substituting the functional group with a phenyl or heterocyclyl group such as pyridyl, furyl, and the like, in the final step. For example, a Thi—Y—O[$R$—$_{R2}$-phenyl] borate can be reacted with a halopyridine to form a compound of I wherein $R_3$ is pyridyl. Alternatively, certain $R_3$ heterocycles are more easily prepared Hin situ by elaborating the functional group on the phenyl ring into the heterocycle. This method is preferred with heterocycles having two or more heteroatoms, such as triazolyl, oxadiazolyl, oxazolyl and the like.

For example, if $R_3$ is a heterocyclic ring, the heterocyclic ring of the compound of Formula I can be prepared from an appropriate $R_1$—$R_2$-functionalized phenoxy-Y-thiadiazole, (or ZO—$R_1$—$R_2$-4-functionalized phenyl moiety wherein Z is (Thi)—Y—). In this method, the heterocycle on the phenoxy ring is elaborated in the final step as described in U.S. Pat. No. 5,075,187 incorporated herein by reference. Suitable substitution of the 4-phenoxy position will depend upon the heterocycle sought in the final roduct. For example, where Het is 1,2,4-oxadiazolyl

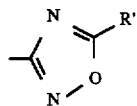

compounds are prepared from either the appropriate 4—Z—O—$R_1$—$R_2$-benzonitrile, where z is —Y—thiadiazole, by reaction with, for example, hydroxylamine hydrochloride in preferably a noninteracting solvent, preferably an alkanol, for example; methanol, ethanol, n-butanol, and the like. The product thus obtained is then reacted with an acid anhydride of formula (R'CO)$_2$O, where R' is alkyl, haloalkyl, and the like; or by an orthoformate or orthoformate ester, if R' is hydroxy or alkoxy. R' appears on the $R_3$ heterocycle of the final product. The reaction occurs between ambient temperature and the boiling point of the reaction mixture in a basic solvent, such as pyridine. The product is a compound of formula I where $R_3$ is 5—R'—1,2,4-oxadiazolyl, other compounds are made by analogy.

The $R_1$—$R_2$—$R_3$-phenols used to prepare compounds of Formula I are known in the art. Typically they are prepared by reaction of a suitably protected phenol having, in the 4 position, a functional group such as cyanide, aldehyde, halide, acid chloride group, as described in U.S. Pat. No. 4,942,241; 4,945,164; 5,051,437; 5,002,960; 5,110,821; 4,939,267; 4,861,971; 4,857,539; 5,242,924; or 4,843,087 each incorporated herein by reference, to obtain the corresponding suitably protected, heterocyclyl phenol which is then deprotected by means well known in the art. Other known phenols likewise can be used to prepare compounds of formula I, for example any 4-phenylphenols, 4-alkoxycarbonylphenols substituted or unsubstituted, as described above can be used.

It is expected that any $R_1$—$R_2$—$R_3$-phenol can be reacted with the hydroxy-Y-thiodiazole or to prepare compounds of formula I.

R' can be manipulated in any way consistent with manipulations of side groups of the heterocycle, for example, replacement of hydroxy with chloro, cleavage of an ether to a hydroxy, others are contemplated.

It will be appreciated that neither the timing of the elaboration of the heterocyclic substituents or pyridazine nor the order of assembly of the intermediates is crucial to the successful synthesis of compounds of Formula I. Thus by judicious choice of reactants one can prepare compounds of Formula I.

Alternatively, where the 4—ZO—$R_1$—$R_2$-benzonitrile with Z as a protecting group, the product is a $R_1$—$R_2$—$R_3$—(heterocyclyl) phenol upon deprotection. This phenol is reacted with the thiadiazolylalkyl halide or thiadiazolyl alkanol or the halo-Y-X or hydroxy-Y-X, wherein the thiadiazole is substituted or elaborated in a later step in the synthesis of a compound of formula I.

Hydroxy Y-thiadiazoles used in the invention are known, commercially available or can be prepared by known methods. For example, commercially available halo-1,2,4-thiadiazoles can be coupled to a w-haloalkenyl ester or haloalkyne ester by standard methods, such as tin-iodide coupling preferably with subsequent reduction to the alkanol by known methods.

Alternatively, 1,3,4-thiadiazolyl alkyl halides, 1,3,4-thiadiazolyl alkanols or $R_1$—$R_2$—$R_3$—phenoxy—Y—1,3,4—thiadiazole compounds can be prepared by reacting a suitable phenoxy-Y-carbazide, with, for example, Lawssen's reagent, under standard conditions, as described above for the preparation of compounds of formula I. The carbazide can be prepared from the reaction of the known phenoxyalkyl acid halide or phenoxyalkyl ester with a R'-hydrazide (where R' forms the substitution or a substitution precursor for the thiadiazole ring).

Simple chemical transformations which are conventional and well known to those skilled in the art of chemistry can be used for effecting changes in functional groups in the compounds of the invention. For example, acylation of hydroxy- or amino-substituted species to prepare the corresponding esters or amides, respectively; alkylation of phenyl or furyl substituents; cleavage of alkyl or benzyl ethers to produce the corresponding alcohols or phenols; and hydrolysis of esters or amides to produce the corresponding acids, alcohols or amines, preparation of anhydrides, acid halides, aldehydes, simple aromatic alkylation, sulfonation of carbazides, formation of chloro or fluoro alkyls from hydroxy alkyls or keto compounds, the displacement of hydroxy by halo on heterocyclic rings, and the formation of other hetercycles and the like as desired can be carried out.

For a complete overview of the common reactions used in heterocyclic chemistry, see for example, Katritzky and Rees *Comprehensive Heterocyclic Chemistry*, or Castle *Heterocyclic Compounds*, or any other comprehensive treatises on the subject.

Moreover, it will be appreciated that obtaining the desired product by some reactions will be better facilitated by blocking or rendering certain functional groups non reactive. This practice is well recognized in the art, see for example, Theodora Greene, *Protective Groups in Organic Synthesis* (1991). Thus when reaction conditions are such that they can cause undesired reactions with other parts of the molecule, the skilled artisan will appreciate the need to protect these reactive regions of the molecule and act accordingly.

Starting materials used to prepare the compounds of Formula I are commercially available, known in the art, or prepared by known methods. Many of the preparations of starting materials herein are incorporated by reference from the patent literature.

EXEMPLARY DISCLOSURE

As used herein $R_1$, $R_2$, $R_3$, $R_4$, X, Y and Het have the same meanings in describing intermediate species as in compounds of formula I.

For the purpose of naming substituents in Formula I, the phenyl ring of any compound of formula I shall be numbered;

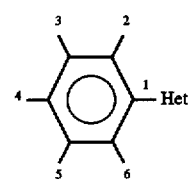

Thus when a compound of formula I has substitution on the phenyl ring, it is referred to by this numbering system regardless of how the compound is actually named. For example, if a compound is prepared and the designation $R_1$,$R_2$=3,5-dimethyl, this means

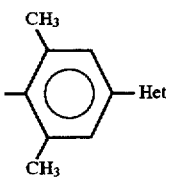

regardless of whether 3,5-dimethyl or 2,6-dimethyl appears in the name of the compound.

For the purpose of naming substituents in compounds of formula I, the 1,3,4-thiadiazole rings described herein shall be numbered

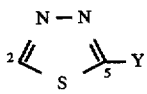

Regardless of the substituent that appears at the 2-position of the 1,3,4-thiadiazolyl, in order to prevent any confusion on the part of the reader who may not be well versed in the art of chemical nomenclature. Therefore;

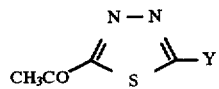

is denoted as 2-acetyl-1,3,4-thiadiazol-5-yl, and

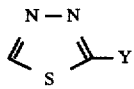

is denoted as 1,3,4-thiadiazol-5-yl, though accepted nomenclature rules may cause the radical to be named differently.

EXAMPLE 1

A. 4-[(4-Cyano-2,6-dimethyl)phenoxy]butyric acid To a solution of 5 g (34 mmol) of 4-cyano-2,6-dimethylphenol in 120 mL of N-methyl-pyrrolidinone was added 5.86 g. (42 mmol) of potassium carbonate, 0.58 g (3 mmol) of potassium iodide, and 4.8 mL (34 mmol) of ethyl 4-bromobutyrate, and the resulting mixture was heated at 60° C. for 24 h. The reaction mixture was cooled, diluted with water, filtered, and a white solid residue was washed with water to afford 8.9 g (quantitative yield) of ethyl 4-[(4-cyano-2,6-dimethyl)phenoxy]butyrate. The above ester was stirred at room temperature with 120 mL of ethanol/water (4:1) containing 820 mg (34 mmol) of LiOH, ethanol was removed in vacuo, and the aqueous layer was washed with water. The aqueous layer was acidified, a white solid was filtered and dried to afford 6.93 g (88%) of 4-[(4-cyano-2,6-dimethyl) phenoxy] butyric acid.

B. t-Butyl N-[4-[(4-cyano-2,6-dimethyl)phenoxy]butyryl] carbazate

To a solution of 4-[(4-cyano-2,6-dimethyl)phenoxy] butyric acid (654 mg, 2.81 mmol) in 15 mL of methylene chloride was added 1.2 mL (16.86 mmol) of thionyl chloride and the mixture was allowed to reflux for 3 h. The mixture was concentrated in vacuo, a pale yellow residual oil in 20 mL of THF was mixed with 409 mg (3.09 mmol) of t-butyl carbazate and few drops of triethylamine, and then the mixture was allowed to reflux for 1.5 h. The reaction mixture was cooled, concentrated in vacuo, diluted with water, and extracted with methylene chloride (x3). The combined organic layer was washed with brine, dried over sodium sulfate, and concentrated in vacuo to afford 899 mg (92%) of t-butul N-[4-[(4-cyano-2,6-dimethyl)phenoxy] butyryllcarbazate.

C. N-[4-[(4-Cyano-2,6-dimethyl)phenoxy]butyryl] hydrazine

A mixture of 6.73 g (19.4 mmol) of t-butyl N-[4-[(4-cyano-2,6-dimethyl)phenoxy]butyroyl]carbazate and 25 mL of trifluoroacetic acid in 100 mL of methylene chloride was allowed to stir at 0° C. for 1 h, and then concentrated in vacuo to dryness. The residue was dissolved in water, washed with ether, and the aqueous layer was made basic (pH 9) with sodium hydroxide solution. The white solid was filtered, washed with water, and dried in vacuo to afford 3.65 g (76.2%) of N-[4-[(4-cyano-2,6-dimethyl)-phenoxy] butyryl]hydrazine.

D. N-Acetyl-N'-[4-[(4-cyano-2,6-dimethyl)phenoxy]-butyryl]hydrazine

To a solution of 4-[(4-cyano-2,6-dimethyl)phenoxy] butyric acid (3.9 g, 16.74 mmol) in 120 mL of methylene chloride was added 6 mL of thionyl chloride and the resulting mixture was allowed to reflux for 3 h, cooled, and concentrated to yield a yellow oil. To the yellow oil was added 120 mL of THF, 1.22 g (16.74 mmol) of acetyl hydrazide, and 5 drops of triethylamine, and the mixture was allowed to reflux for 3 h. The mixture was cooled, a white solid was filtered, washed with water, and dried in vacuo, to afford 3.5 g (42%) of N-acetyl-N-[4-[(4-cyano-2,6-dimethyl)phenoxy]butyryl]hydrazine.

E. 2-Methyl-5-13-(4-cyano-2,6-dimethylphenoxy)propyl-1,3,4-thiadiazole

To a solution of 2.79 g (6.92 mmol) of Lawesson's reagent in 150 mL of THF was added 1.57 g (5.43 mmol) of N-acetyl-N'-4-[(4-cyano-2,6-dimethyl)phenoxy]butyryl] hydrazine and the mixture was refluxed for 3 h and then heated at 600° C. overnight. The reaction mixture was concentrated in vacuo, the residue was purified by a silica flash column chromatography (60% ethyl acetate/hexane) to yield 700 mg of a yellow oil which was further purified via recrystallization from ethyl acetate/hexane followed by flash chromatography (hexane/ethyl acetate) to afford 750 mg (48%) of 2-methyl-5-[3-(4-cyano-2,6-dimethylphenoxy) propyl]-1,3,4-thiadiazole.

F. 2-Methyl-5-[3-(4-aminohydroximinomethyl-2,6-dimethylphenoxy)propyl]-1,3,4-thiadiazole To a solution of 2-methyl-5-[3-(4-cyano-2,6-dimethylphenoxy)propyl]-1,3,4-thiadiazole (0.69 g, 2.4 mmol) in 75 mL of ethanol was added 1.65 g (12 mmol) of potassium carbonate and 0.34 g (12 mmol) of hydroxylamine hydrochloride and the mixture was stirred at 500° C. for 14 h. The mixture was filtered, the residue was washed with hot ethanol several times, and the filtrate was concentrated in vacuo to yield 0.98 g of 2-methyl-5-[3-(4-aminohydroximinomethyl-2,6-dimethylphenoxy)-propyl]-1,3,4-thiadiazole, m.p. 79°–80° C.

G. 2-Methyl-5-[3-[4-(5-methyl-1,2,4-oxadiazol-3-yl)-2,6-dimethylphenoxy]-propyl]-1,3,4-thiadiazole (y=1,3-propylene), $R_1=R_2=3,5$-dimethyl, Thi=2-methyl-1,3,4-thiadiazol-5-yl, $R_3=5$-methyl-1,2,4-oxadiazolyl)

To a solution of 2-methyl-5-[3-(4-aminohydroximinomethyl-2,6-dimethyl-phenoxy)propyl]-1,3,4-thiadiazine (980 mg) in 10 mL of pyridine was added 0.3 mL (4.2 mmol) of acetyl chloride, and the resulting mixture was refluxed for 1 h, cooled, and diluted with water. The mixture was extracted with ethyl acetate (x4), the organic layer was washed with an aqueous HCl solution, and brine, and dried over sodium sulfate. The organic layer was concentrated in vacuo and a yellow residual oil was purified by MPLC (75% ethyl acetate in hexane) to afford 342 mg (42%) of 2-ethyl-5-[3-[4-(5-methyl -1,2,4-oxadiazol-3-yl)-2,6-dimethylphenoxy]propyl]-1,3,4-thiadiazole, as a white crystalline solid, m.p. 83°–84° C. (from ether/pentane).

EXAMPLE 2

A. N-Propionyl-N'-[4-[(4-cyano-2,6-dimethyl)phenoxy]butyryl]hydrazine

To a solution of N-[4-[(4-cyano-2,6-dimethyl)phenoxy]butyryl-hydrazine (2.3 g, 9.31 mmol prepared according to the method of example 1) in THF was added 0.81 mL (9.31 mmol) of propionyl chloride and 1 mL of triethylamine and the resulting mixture was stirred at room temperature for 2 h. The mixture was concentrated in vacuo, the white solid product was triturated with water, filtered, washed with ether, and dried to afford 2.569 g (91%) of N-propionyl-N'-[4-[(4-cyano-2,6-dimethyl)phenoxy]butyryl]hydrazine.

B. 2-Ethyl-5-[3-(4-cyano-2,6-dimethylphenoxy)propyl]-1,3,4-thiadiazole

To a suspension of 2.58 g (8.51 mmol) of N-propionyl-N'-[4-[(4-cyano-2,6-dimethyl)phenoxy]butyryl]hydrazine in 200 mL of dry THF was added 3.44 g (8.51 mmol) of Lawesson's reagent and the mixture was allowed to reflux for 20 h. The reaction mixture was concentrated in vacuo, and a yellow residual oil was purified by short silica column flash chromatography (hexane/ethyl acetate, 2:1) and MPLC (hexane/ethyl acetate, 1:1) to afford 2.09 g (82%) of 2-ethyl-5-[3-(4-cyano-2, 6-dimethylphenoxy)propyl]-1,3,4-thiadiazole.

C. 2-Ethyl-5-[3-(4-aminohydroximinomethyl-2,6-dimethylphenoxy)propyl]-1,3,4-thiadiazole To a solution of 2-ethyl-5-[3-(4-cyano-2,6-dimethylphenoxy)propyl]-1,3,4-thiadiazole (1.6 g, 5.32 mmol) in ethanol was added 3.67 g (26.58 mmol) of potassium carbonate and 1.85 g (26.58 mmol) of hydroxylamine hydrochloride and the mixture was stirred at room temperature for 1.5 days. The mixture was filtered, and the filtrate was concentrated in vacuo to yield 1.12 g of 2-ethyl-5-[3-(4-aminohydroximinomethyl-2 6-dimethyphenoxy)propyl]-1,3,4-thiadiazole, m.p. 158°–160° C.

D. 2-Ethyl-5-[3-[4-(5-difluoromethyl-1,2,4-oxadiazol-3-yl)-2,6-dimethylphenoxy]propyl]-1,3,4-thiadiazole (Y=1,3-propylene, R$_1$=R$_2$=3,5-dimethyl, Thi=2-ethyl-1,3,4-thiadiazole, R$_3$=5-difluoromethyl-1,2,4-oxadiazole-3-yl)

To a solution of 2-ethyl-5-[3-(4-aminohydroximinomethyl-2,6-dimethylphenoxy) -propyl]-1,3,4-thiadiazole (800 mg, 2.4 mmol) in N-methylpyrrolidinone (3 mL) was added 1.44 mL (14.46 mmol) of ethyl difluoroacetate, and the resulting mixture was heated at 95° C. for 4 h, cooled, and diluted with water. The mixture was extracted with ethyl acetate (x4), the organic layer was washed with water, and brine, and dried over sodium sulfate. The organic layer was concentrated in vacuo and the residue was purified by MPLC (25%–40% ethyl acetate in hexane) to afford 500 mg (55%) of 2-ethyl-5-[3-[4-(5-difluoromethyl-1,2,4-oxadiazol-3-yl)-2,6-dimethylphenoxy]-propyl]-1,3,4-thiadiazole, as a white crystalline solid, m.p. 83°–84° C. (from methylene chloride and hexane).

EXAMPLE 3

A. To a 0° C. solution of ethyl succinyl chloride (25 g) in 300 mL of CH$_2$Cl$_2$ was added 13.2 g of propionylhydrazide in a mixture of 100 ML CH$_2$Cl$_2$ and 27.4 ML of diisopropylethylamine, dropwise. The mixture was stirred at room temperature for 2 h. The mixture was quenched with water, extracted with ethylene chloride, and the organic layer was dried and concentrated in vacuo. The above solid was recrystallized from EtOAC/hexane (5:1) to afford N-propionyl-N'-(ethyl)succinyl hydrazide.

B. 28.1 g of the product of example 3A was dissolved in 2 L THF. 89.8 g of P$_4$S$_{10}$ was added and the mixture was refluxed for 2 h. Upon cooling, 800 mL of 5% sodium carbonate solution and 1L ether was added and the mixture was filtered. The filtrate was separated and the aqueous layer extracted with 750 mL Et$_2$O. The organic layer was dried over MgSO$_4$ and concentrated in vacuo, to yield 22.7 g (53%) of ethyl 3-(5-ethyl-1,3,4-thiadiazol-2-yl) propionate.

C. 112 mL of 1μ LAH (in ether) cooled at −20° C. under nitrogen. An equimolar amount (24 g) of the propionate prepared by the method of 3B was added dropwise as a suspension (in ether) and stirred for 15 minutes. The reaction was quenched with water and base. Upon workup 3-(5-ethyl-1,3,4-thiadiazol-2-yl) propanol (13.46 g) was obtained in 78% yield, the product was vacuum (0.1 mm Hg) distilled at 130°–140° C. before the next step.

D. 9.7 g of 2,6-dimethyl-4(5-difluoromethyl-1,2,4-oxadiazol-3-yl)phenol described in allowed U.S. patent application Ser. No. 07/869,287 incorporated herein by reference, and 15.7 g of triphenyl phosphine and 6.9 g of the propanol were taken up in 80 ml THF. The mixture was cooled to <5° C. 10.4 g DEAD in 80 ml THF was added dropwise under nitrogen and the mixture was stirred 1 hour. The solution was poured into hexane and stirred until a gummy-solid formed. The mixture was filtered to remove solids. The solution was concentrated in vacuo to a pale-yellow solid. The crude was purified by column chromatography, yielding a compound of formula I, 2-Ethyl-5-[5-[4-(5-difluoromethyl-1,2,4-oxadiazol-3-yl)-2,6-dimethylphenoxy]-propyl]-1,3,4-thiadiazole (Y=1,3-propylene, R$_1$, R$_2$=3,5-dimethyl, Thi=2-ethyl -1,3,4-thiadiazol-5yl R$_3$=5-difluoromethyl-1, 2,4-oxadiazol -3-yl) m.p. 84° C.

EXAMPLE 4

A. Methyl N-[4-[(4-cyano-2,6-dimethyl)phenoxy]butyroyl] carbazate

To a solution of 4-[(4-cyano-2,6-dimethyl)phenoxy] butyric acid (247 mg, 1.06 mmol) in 15 mL of methylene chloride was added 0.4 mL (5.48 mmol) of thionyl chloride and the mixture was allowed to reflux for 3 h. The mixture was concentrated in vacuo, and the residual oil in 20 mL of THF was mixed with 104 mg (1.16 mmol) of methyl carbazoate and 3 drops of triethylamine, and then the mixture was allowed to reflux for 2 h. The reaction mixture was cooled, concentrated in vacuo, diluted with water, and a white solid product was filtered and dried to afford 275 mg of methyl N-[4-[(4-cyano -2,6-dimethyl)-phenoxy]butyroyl] carbazate, m.p. 154°–155° C.

B. 2-Oxo-5-[3-(4-cyano-2,6-dimethylphenoxy)propyl]-2,3-dihydro-1,3,4-thiadiazole To a solution of 1.72 g (5.65 mmol) of methyl N-[4-[(4-cyano-2,6-dimethyl)phenoxy]butyroyl]carbazate in 100 mL of THF was added 2.22 g (5.50 mmol) of Lawesson's reagent and the mixture was allowed to reflux overnight. The reaction mixture was concentrated in vacuo, and the yellow residual oil was purified by MPLC (hexane/ethyl acetate, 1:1) to afford 0.406 g (24.5%) of 2-oxo-5-r3-(4-cvcano-2,6-dimethylhenoxy)propyl-1,3,4-thiadiazol -3H-2-one.

C. 2-Oxo-5-[3-(4-aminohydroximinomethyl-2,6-dimethylphenoxy)propyl]-1,3,4-thiadiazol-3H-2

To a solution of 2-oxo-5-[3-(4-cyano-2,6-dimethylphenoxy)propyl]-2,3-dihydro-1,3,4-thiadiazole (801 mg, 2.77 mmol) in 75 mL of ethanol was added 963 mg (13.86 nmol) of hydroxylamine hydrochloride and 191.3 mg (13.86 mmol) of potassium carbonate and the the mixture was stirred at room temperature overnight. The mixture was filtered and the filtrate was concentrated in vacuo to yield 826 mg (93%) of 2-oxo-5-[3-(4-aminohydroximinomethyl-2 6-dimethylphenoxy)propyl]-1,2-dihydro-1,3,4-thiadiazole.

D. 2-Oxo-5-[3-[4-(5-difluoromethyl-1,2,4-oxadiazol-3-yl)-2,6-dimethylphenoxy]propyl]-1,2-dihydro-1,3,4-thiadiazole (Thi=2-hydroxy-1,3,4-thiadiazol-5-yl; $R_1=R_2=3,5$-dimethyl; Y=1,3-propylene; $R_3$=5-difluoromethyl-1,2,4-oxadiazol-3yl)

To a solution of 2-oxo-5-[3-(4-aminohydroximinomethyl-2,6-dimethyl-phenoxy)propyl]-1,2-dihydro-1,3,4-thiadiazole (700 mg, 2.17 mmol) in N-methyl-pyrrolidinone (3 mL) was added 1.3 mL (13.02 mmol) of ethyl difluoroacetate, and the resulting mixture was heated at 90° C. overnight. The mixture was cooled, diluted with water, and extracted with methylene chloride (x4). The organic layer was washed with brine, and dried over sodium sulfate. The organic layer was concentrated in vacuo and the residual brown oil was purified by MPLC (25%-35% ethyl acetate in hexane) to afford 637 mg (67%) of 2-oxo-5-[3-[4-(5-difluoromethvl-1,2,4-oxadiazol-3-yl)-2,6-dimethylphenoxy]propyl]-1,2-dihydro- 1,3,4-thiadiaole. m.p. 110°–111° C. (recrystallization from methylene chloride/hexane.

EXAMPLE 5

The following compounds of the invention were prepared according to the methods described above:

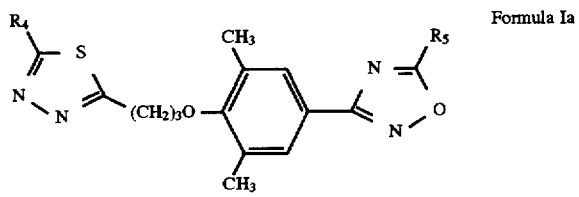

Formula Ia wherein Y is 1,3-propylene, $R_1,R_2$=3,5-dimethyl, $R_3$=5-$R_5$-1,2,4-oxadiazol-3-yl; Thi=2-$R_4$-1,3,4-thiadiazolyl

| Ex. | $R_4$ | $R_5$ | M.P. (C) |
|---|---|---|---|
| 5a | methyl | trifluoromethyl | 66–67 |
| 5b | methyl | difluoromethyl | 75–76 |
| 5c | ethyl | trifluoromethyl | 47–48 |
| 5d | n-propyl | difluoromethyl | 69–71 |
| 5e | n-butyl | difluoromethyl | — |
| 5f | cyclopropyl | difluoromethyl | 110–111 |
| 5g | trifluoromethyl | methyl | 84–85 |
| 5h | methoxymethyl | difluoromethyl | 92–93 |
| 5i | hydroxymethyl | $CF_2H$ | 92–93 |
| 5j | methyl | trifluoromethyl | 38–40 |
| 5k | 2,2-difluoroethyl | difluoromethyl | 74–75 |
| 5l | difluoromethyl | difluoromethyl | 72–73 |
| 5m | acetyl | difluoromethyl | 90–91 |
| 5n | methoxy | difluoromethyl | 83–84 |
| 5o | Chloro | difluoromethyl | 89–90 |

The following compounds of formula 1b were made;

Formula 1b

| Ex. | n= | $R_1$ | $R_2$ | M.P. |
|---|---|---|---|---|
| 5p | 3 | H | H | 75–76 C. |
| 5q | 3 | $CH_3$ | H | 74–76 C. |
| 5r | 5 | $CH_3$ | $CH_3$ | 54–55 C. |

EXAMPLE 6

A. 3-Methyl-5-tributyltin-1,2,4-thiadiazole

To a cooled (−95° C., under liq. nitrogen and hexane) solution of 3-methyl-5-bromo-1,2,4-thiadiazole (9.4 g, 52.5 mmol) in 200 mL of THF was added 61.8 mL (105 mmol) of 1.7 N-butyllithium dropwise at −90° C. The resulting pink solution was stirred for an additional 15 min, and then 17.8 g (55 mmol) of tributyltin chloride was added dropwise at −90° C. The cold solution was allowed to warm to 0° C. and then quenched with ammonium chloride solution. The reaction mixture was extracted with ether, the organic layer was dried over sodium sulfate, and concentrated in vacuo to afford 3-methyl-5-tributyltin-1,2,4-thiadiazole.

B. Ethyl b-(3-methyl-1,2,4-thiadiazol-5-yl)acrylate

To a solution of 3-methyl-5-tributyltin-1,2,4-thiadiazole (49 mmol) in 160 mL of xylene was added 11 g (49 mmol) of ethyl b-(iodo)acrylate followed by $Pd(PPh_3)_4$ (2.2 g, 2.45 mmol). The mixture was heated at 120° C. for 18 h, cooled, and saturated aqueous KF solution was added. The mixture was filtered (filter paper), the residue was washed with ethyl acetate, and the aqueous layer was extracted with ethyl acetate (3x). The combined organic layer was dried over sodium sulfate and concentrated in vacuo. The residue was purified by silica chromatography (10 cm column, methylene chloride/acetone from 15/1 to 1/6) and rechromatography (10 cm silica column, ethyl acetate/hexane 1/5) to yield 2 g (21 %) of ethyl b-(3-methyl-1,2,4-thiadiazol-5-yl)acrylate, as a white solid (recrystallization from ethyl acetate/hexane). The acrylate was then reduced to the alcohol with LAH and the saturated alkyl was prepared with palladium carbon and hydrogen.

C. 3-Methyl-5-[3-[4-(5-difluoromethyl-1,2,4-oxadiazol-3-yl)-2,6-dimethylphenoxy]propyl]-1,2,4-thiadiazole *I, Thi=3-methyl-1,2,4-thiadiazol-5-yl, Y=1,3-propylene, $R_1=R_2$=methyl, $R_3$=5-difluoromethyl-1,2,4-oxadiazol-3-yl)

A mixture of 5-(3-hydroxypropyl)-3-methyl-1,2,4-thiadiazole (242 mg, 1.53 mmol), 4-(5-difluoromethyl-1,2,4-oxadiazol-3-yl)-2,6-dimethylphenol described in allowed in U.S. patent application Ser. No. 07/869,287, incorporated herein by reference (400 mg, 1.67 mmol), and DEAD (290 mg, 1.67 mmol) was dissolved in 16 mL of THF. To the above solution was added triphenylphosphine (438 mg, 1.67 mmol) at 0° C. and the mixture was allowed to warm to 20° C. overnight. The solvent was removed in vacuo, an aqueous sodium bicarbonate solution was added, and the mixture was extracted with methylene chloride (7x). The organic layer was dried over sodium sulfate and concentrated in vacuo. The residue was purified by silica column chromatography (10 cm column, ethyl acetate/hexane, from 1/6 to 1/4) followed by recrystallization from ethyl acetate/hexane to afford 471 mg (81%) of 3-methyl-5-r3-[4-(5-difluoromethyl-1,2 4-oxadiazol-3-yl)-2,6-dimethyl-phenoxy-1,2,4-thiadiazole, as a white crystalline solid, m.p. 62°–64° C.

D. 3-Methyl-5-[3-[4-(5-methyl-1,2,4-oxadiazol-3-yl)-2,6-dimethylphenoxy]-propyl]-1,2,4-thiadiazole (I, Thi=3-methyl -1,2,4-thiadiazol-5-yl, Y=1,3-propylene, $R_1=R_2=$ methyl, $R_3$=5-methyl-1,2,4-oxadiazol-3-yl)

A mixture of 5-(3-hydroxypropyl)-3-methyl-1,2,4-thiadiazole (66 mg, 0.42 mmol), 4-(5-methyl-1,2,4-oxadiazol-3-yl)-2,6-dimethylphenol (94 mg, 0.46 mmol), and DEAD (80 mg, 0.46 mmol) was dissolved in 5 mL of THF. To the above solution was added triphenylphosphine (120 mg, 0.46 mmol) at 0° C. and the mixture was allowed to warm to 200° C. overnight. The solvent was removed in vacuo, an aqueous sodium bicarbonate solution was added, and the mixture was extracted with methylene chloride (3x). The organic layer was dried over sodium sulfate and concentrated in vacuo. The residue was purified by silica column chromatography (20 cm column, ethyl acetate/hexane, from ⅙ to ¼) followed by recrystallization from ethyl acetate/hexane to afford 88 mg (61%) of 3-methyl-5-[3-[4-(5-methyl-1,2,4-oxadiazol-3-yl -2,6-dimethylphenoxy]proyyl]-1,2,4-thiadiazole, as a white crystalline solid, m.p. 67+≅71° C.

EXAMPLE 7

As further examples, phenols described only generally thus far can be reacted with any known thiadiazolyl alkanol, thiadiazolyl alkyl halide or any of those described herein using the methods previously described herein to provide a compound of formula I. It is contemplated that any phenol disclosed in allowed application Ser. No. 07/869,287, incorporated herein by reference, is elaborated to a thiadiazole of formula I, using the methods described above. For the reader's convenience the same nomenclature conventions described herein for compounds of formula I are adhered to, and a literature reference describing the known phenol is included.

| $R_1$ | $R_2$ | $R_3$ | Reference U.S. Pat. No. |
|---|---|---|---|
| H | H | 1,2,4-oxadiazol-2yl | 4,857,539 |
| H | H | 4,2-dimethyl-2-thiazolyl | 4,857,539 |
| H | H | 2-benzoxazolyl | 4,857,539 |
| 3,5 dichloro | | 3-furanyl | 4,857,539 |
| 3,5 dichloro | | 2-furanyl | 4,857,539 |
| 3,5 dichloro | | 2-thienyl | 4,857,539 |
| 3,S dichloro | | 2-pyridinyl | 4,857,539 |
| 3,5 dichloro | | 1-methyl-1H-pyrrol-2yl | 4,857,539 |
| 3,5 dichloro | | 3-thienyl | 4,857,539 |
| 3,5 dichloro | | 4-pyridinyl | 4,857,539 |
| 3 nitro | H | benzothiazol-2-yl | 4,857,539 |
| H | H | 2-(4,5-dihydro-4 methyl)oxazolyl | 4,843,087 |
| 3 methyl | H | 2-oxazolyl | 4,843,087 |
| 3 bromo | H | 2-oxazolyl | 4,843,087 |
| 3,5 dimethyl | | 3-methyl-5-isoxazolyl | 4,843,087 |
| 2,6 dimethyl | | 3-methyl-5-isoxazolyl | 4,843,087 |
| H | H | 5-methyl-3-isoxazolyl | 4,942,241 |
| H | H | 4-hydroxy phenyl | (Aldrich) |
| H | H | phenyl | (Aldrich) |
| H | H | 5-ethyl-thiazol-2-yl | 5,100,893 |
| H | H | 4,5-dimethyl-thiazol-2-yl | 5,100,893 |
| H | H | 2-ethyl-thiazol-4-yl | 5,100,893 |
| H | H | 5-ethyl-1,3,4-thiadiazol-2-yl | 5,100,893 |
| H | 3-Cl | 3-ethyl-1,2,4-oxadiazol-5-yl | 5,100,893 |
| H | H | 3-cyclopropyl-1,2,4-oxadiazol-5-yl | 5,100,893 |
| H | H | 3-tbutyl-1,2,4-oxadiazolyl | 5,100,893 |
| H | H | 5-ethyl-1,3,4-oxadiazol-2-yl | 5,100,893 |
| H | H | 3-cyclopropyl,2,4-oxadiazol-5-yl | 5,100,893 |
| H | H | 3-ethyl-1,3,4-thiadiazol-5-yl | 5,100,893 |
| H | H | 3-(2hydroxy)propyl-1,2,4-oxadiazol-5-yl | 5,100,893 |
| H | H | 4-ethyl-3-thiazol-2-yl | 5,100,893 |
| H | H | 5-ethyl-3-thiazol-2-yl | 5,100,893 |
| 3-chloro | H | 3-ethyl-1,2,4-oxadiazol-5-yl | 5,100,893 |
| H | H | 4,5-dimethyl-3-thiazol-2-yl | 5,100,893 |
| 2-methoxy | H | 4,5dihydro oxazol-2-yl | 4,843,087 |
| 3-methoxy | H | 4,5dihydro oxazol-2-yl | 4,843,087 |
| 3-chloro | H | 4,5dihydro oxazol-2-yl | 4,843,087 |
| 3-hydroxy | H | 4,5dihydro oxazol-2-yl | 4,843,087 |
| 3,5 di-t-butyl | | 4,5dihydro oxazol-2-yl | 4,843,087 |
| 3-difluoromethyl | H | 4,5dihydro oxazol-2-yl | 4,843,087 |
| 3-hydroxymethyl | H | 4,5dihydro oxazol-2-yl | 4,843,087 |
| 3-carboxy | H | 4,5dihydro oxazol-2-yl | 4,843,087 |
| 2-methyl | 3-hydroxy | 4,5dihydro oxazol-2-yl | 4,843,087 |
| 2,6 dichloro | | 4,5dihydro oxazol-2-yl | 4,843,087 |
| 3,5 difloro | | 4,5dihydro oxazol-2-yl | 4,843,087 |
| 3-chloro | 5-ethynyl | 4,5dihydro oxazol-2-yl | 4,843,087 |

EXAMPLE 8

It is contemplated that 4-hydroxy-3,5-dimethylbenzonitrile can be reacted with hydroxlamine hydrochloride using the conditions of Example 2C and the resulting product can be reacted then with ethyl chloro formate and acetone. Upon work-up providing a compound wherein Y=1,3-propylene, providing a phenol where $R_1$ and $R_2$=3,5-dimethyl, $R_3$=5-hydroxy-1,2,4-oxadiazol-3-yl. This mphenol may be reacted with any of the preceeding thiadiazolyl alkanols to form compounds of formula I.

B. The compound described above may be reacted with phosphorus oxychloride pyridine (over a base trap) upon refluxing (approximately 4 hours) one obtains a 5-chloro-1,2,4-oxadiazol-3-yl compound of formula I.

BIOLOGICAL EVALUATION

Biological evaluation of representative compounds of formula I has shown that they possess antipicornaviral activity. They are useful in inhibiting picornavirus replication in vitro and are primarily active against picornaviruses, including enteroviruses, echovirus and coxsackie virus, especially rhinoviruses. The in vitro testing of the representative compounds of the invention against picornaviruses showed that viral replication was inhibited at minimum inhibitory concentrations (MIC) ranging from 0.05 to 7.4 micrograms per milliliter (µg/mL).

The MIC values were determined by an automated tissue culture infectious dose 50% (TCID-50) assay. HeLa cells in monolayers in 96-well cluster plates were infected with a dilution of picornavirus which had been shown empirically to produce 80% to 100% cytopathic effect (CPE) in 3 days in the absence of drug. The compound to be tested was serially diluted through 10, 2-fold cycles and added to the infected cells. After a 3 day incubation at 33° C. and 2.5% carbon dioxide, the cells were fixed with a 5% solution of glutaraldehyde followed by staining with a 0.25% solution of crystal violet in water. The plates were then rinsed, dried, and the amount of stain remaining in the well (a measure of intact cells) was quantitated with an optical density reader. The MIC was determined to be the concentration of compound which protected 50% of the cells from picornavirus-induced CPE relative to an untreated picornavirus control.

In the above test procedures, representative compounds of formula I were tested against some the serotypes from a panel of 10 human rhinovirus (HRV) serotypes, namely HRV-3, -4, -5, -9, -16, -18, -38, -66, -75 and -67, (noted in the table as panel B) and the MIC value, expressed in micromolar concentration, for each rhinovirus serotype was determined for each picornavirus. Then $MIC_{50}$ and $MIC_{80}$ values, which are the minimum concentrations of the compound required to inhibit 50% and 80%, respectively, of the tested serotypes were determined. The compounds tested were found to exhibit antipicornaviral activity against one or more of these serotypes.

The following Table gives the test results for representative compounds of the invention. The panel of picornaviruses used in the test appears before the $MIC_{80}$ and $MIC_{50}$ figure and the number of serotypes which the compound is tested against (N) is indicated after the $MIC_{80}$ and $MIC_{50}$ figure.

TABLE

| Ex | $Mic_{50}$ | $Mic_{80}$ | N |
| --- | --- | --- | --- |
| 1g | 0.11 | 1.0 | 10 |
| 2d | 0.031 | 0.043 | 10 |
| 3d | 0.040 | 0.043 | 10 |
| 4d | 0.34 | >4.2 | 10 |
| 5a | 0.095 | 0.43 | 9 |
| 5b | 0.066 | 0.14 | 10 |
| 5c | 0.092 | 0.41 | 10 |
| 5d | 0.25 | 0.68 | 10 |
| 5e | 0.40 | >7.4 | 10 |
| 5f | 0.042 | 0.13 | 10 |
| 5g | 0.25 | 0.57 | 10 |
| 5h | 0.076 | 0.71 | 10 |
| 5i | 0.15 | 3.5 | 10 |
| 5j | 1.8 | >4.0 | 9 |
| 5k | 0.24 | 0.56 | 9 |
| 5l | 0.15 | 0.65 | 10 |
| 5m | 0.17 | 1.4 | 10 |
| 5n | 0.055 | 0.30 | 9 |
| 5o | .24 | 1.2 | 10 |
| 5p* | >1.1 | >1.1 | 10 |
| 5q | 1.5 | >4.2 | 9 |
| 6c | 0.92 | 1.6 | 9 |
| 6d | 1.8 | >4.6 | 10 |

*Active against 4 serotypes

Example 3d was also tested against 101 Human Rhinoviruses; 1a, 1b, and 3–100 (except HRV 74) using the protocol described above. $Mic_{50}$ and $Mic_{80}$ for example 3d were 0.04 µM and 0.19 µM respectively.

Preliminary data indicate that example 3d provides excellent in vitro and in vivo protection against coxsackie virus B3. Using the protocol described above example 3d gave a $Mic_{50}$ of 0.001 µg/ml in vitro.

The preliminary data indicates that PD50 (the protective dose to prevent death in 50% of an infected mouse population) is of a range that makes the example useful in preventing coxsackie virus infection, in infected mammals, preventing death due to the infection.

Preliminary bioavailability data obtained in dogs, suggests that the bioavailability for example 3d is very good. Its solubility is 1.1 mg/ml in simulated gastric fluid, and 0.63 mg/ml in simulated intestinal fluid.

FORMULATIONS

The compounds of formula I can be formulated into compositions, including sustained release compositions together with one or more non-toxic physiologically acceptable carriers, adjuvants, or vehicles which are collectively referred to herein as carriers, in any conventional form, using conventional formulation techniques for preparing compositions for treatment of infection or for propylactic use, using formulations well known to the skilled pharmaceutical chemist, for parenteral injection or oral or nasal administration, in solid or liquid form, for rectal or topical administration, or the like.

The compositions can be administered to humans and animals either orally, rectally, parenterally (intravenous, intramuscularly, or subcutaneously), intracisternally, intravaginally, intraperitoneally, locally (powders, ointments or drops), or as an aerosal, for example as a nasal or a buccal spray.

Compositions suitable for parenteral injection can comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, polyalkylene glycols, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents that delay absorption, for example, aluminum monostearate and gelatin.

Solid dosage forms for oral administration include capsules, tablets, pills, powders, lozenges, and granules which may be dissolved slowly in the mouth, in order to bathe the mouth and associated passages with a solution of the active ingredient. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glylcerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as, for example, quaternary ammonium compounds, (g) wetting agents, as for example, cetyl alcohol and glycerol monostearate, (h) adsorbents, as, for example, kaolin and bentonite, and (i) lubricants, as, for example, talc, calcium stearate, magnesium stearate, solid polyethylene glycols, sodium lauryl sulfate or mixtures thereof. In the case of capsules, tablets, and pills, the dosage forms can also comprise buffering agents.

Certain solid dosage forms can be delivered through the inhaling of a powder manually or through a device such as a SPIN-HALER used to deliver disodium cromoglycate (INTAL). When using the latter device, the powder can be encapsulated. When employing a liquid composition, the drug can be delivered through a nebulizer, an aerosol vehicle, or through any device which can divide the composition into discrete portions, for example, a medicine dropper or an atomizer.

Solid compositions of a similar type may also be formulated for use in soft and hard gelatin capsules, using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They can contain opacifying agents, and can also be of such composition that they release the active compound or compounds in a certain part of the intestinal tract in a delayed manner.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. Also solid formulations can be prepared as a base for liquid formulations. In addition to the active compounds, the liquid dosage forms can contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, particularly cottonseed oil, ground-nut oil, corn germ oil, olive oil, castor oil, and sesame oil, glycerol, tetrahydrofurfuryl alcohol, polyethyleneglycols, and fatty acid esters of sorbitan or mixtures of these substances, and the like. Besides such inert diluents, the composition can also include adjuvants, such as wetting-agents, emulsifying and suspending agents, sweetening, flavoring, and perfuming agents.

Suspensions, in addition to the active compounds, can contain suspending agents, as for example, ethoxylated isostearyl alcohols, polyoxyethylene sorbitol5, polyethyleneglycols of varying molecular weights and sorbitan esters, microcrystalline cellulose, aluminum metahydroxide, bentonite, agar-agar and tragacanth, or mixtures of these substances, and the like.

Compositions for rectal or vaginal administration are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and, therefore, melt in the rectum or vaginal cavity and release the active component.

Compositions for administration as aerosols are prepared by dissolving a compound of Formula I in water or a suitable solvent, for example an alcohol ether, or other inert solvent, and mixing with a volatile propellant and placing in a pressurized container having a metering valve to release the material in usefule droplet size.

The liquefied propellant employed typically one which has a boiling point below ambient temperature at atmospheric pressure. For use in compositions intended to produce aerosols for medicinal use, the liquefied propellant should be non-toxic. Among the suitable liquefied propellants which can be employed are the lower alkanes containing up to five carbon atoms, such as butane and pentane, or a alkyl chloride, such as methyl, ethyl, or propyl chlorides). Further suitable liquefied propellants are the fluorinated and fluorochlorinated alkanes such as those which are sold under the trademarks "Freon" and "Genetron". Mixtures of the above mentioned propellants can suitably be employed.

Preferred liquefied propellants are chlorine free propellants, for example 134a (tetrafluoroethane) and 227c (heptafluoropropane) which can be used as described above. Typically, one uses a cosolvent, such as an ether, alcohol, or glycol in such aerosol formulations.

The specifications for unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are capsules adapted for ingestion or, aerosols with metered discharges, segregated multiples of any of the foregoing, and other forms as herein described.

Compounds of the invention are useful for the prophylaxis and treatment of infections of suspected picornaviral etiologies such as aseptic meningitis, upper respiratory tract infection, enterovirus infections, coxsackievirus, enteroviruses, and the like. An effective but non-toxic quantity of the compound is employed in treatment. The dosage of the compound used in treatment depends on the route of administration, e.g., intranasal, intrabronchial, and the potency of the particular compound.

Dosage forms for topical administration include ointments, powders, sprays, and inhalants. The active component is admixed under sterile conditions with a physiologically acceptable carrier and any preservatives, buffers, or propellants as may be required. Opthalmic formulations, eye ointments, powders, and solutions are also contemplated.

It will be appreciated that the starting point for dosage determination, both for prophylaxis and treatment of picornaviral infection, is based on a plasma level of the compound at roughly the minimum inhibitory concentration levels determined for a compound in the laboratory. For example, a MIC of 1 µg/mL would give a desired starting plasma level of 0.1 mg/dl and a dose for the average 70 Kg mammal of roughly 5 mg. It is specifically contemplated that dosage range may be from 0.01–1000 mg.

Actual dosage levels of the active ingredient in the compositions can be varied so as to obtain an amount of active ingredient that is effective to obtain a desired therapeutic response for a particular composition and method of administration. The selected dosage level therefore depends upon the desired therapeutic effect, on the route of administration, on the desired duration of treatment, and other factors and is readily determined by those skilled in the art.

The formulation of a pharmaceutical dosage form, including determination of the appropriate ingredients to employ in formulation and determination of appropriate levels of active ingredient to use, so as to achieve the optimum bioavailability and longest blood plasma halflife and the like, is well within the purview of the skilled artisan, who normally considers in vivo dose-response relationships when developing a pharmaceutical composition for therapeutic use.

Moreover, it will be appreciated that the appropriate dosage to achieve optimum results of therapy is a matter well within the purview of the skilled artisan who normally considers the dose-response relationship when developing a regiment for therapeutic use. For example the skilled artisan may consider in vitro minimum inhibitory concentrations as a guide to effective plasma levels of the drug. However, this and other methods are all well within the scope of practice of the skilled artisan when developing a pharmaceutical.

It will be understood that the specific dose level for any particular patient will depend upon a variety of factors including the body weight, general health, sex, diet, time and route of administration, rates of absorption and excretion, combination with other drugs, and the severity of the disease being treated and is readily determined by the skilled clinician.

When administered prior to infection, that is, prophylactically, it is preferred that the administration be within about 0 to 48 hours prior to infection of the host animal with the pathogenic picornavirus. When administered therapeutically to inhibit an infection it is preferred that the administration be within about a day or two after infection with the pathogenic virus.

The dosage unit administered will be dependent upon the picornavirus for which treatment or prophylaxis is desired, the type of animal involved, its age, health, weight, extent of infection, kind of concurrent treatment, if any, frequency of treatment, and the nature of the effect desired.

The compound of the invention also finds utility in preventing the spread of picornaviral infection. The compounds can be used in aerosol sprays applied to contaminated surfaces, to disposable products, such as tissues and the like used by an infected person. In addition the compounds can be used to impregnate household products such as tissues, other paper products, disposable swabs, and the like to prevent the spread of infection by inactivating the picornavirus.

Because compounds of the invention are able to suppress the growth of picornaviruses when added to a medium in which the picornavirus is growing, it is specifically contemplated that compounds of the invention can be used in disinfecting solutions, for example in aqueous solution with a surfactant, to decontaminate surfaces on which polio, Coxsackie, rhinovirus, and/or other picornaviruses are present, such surfaces including, but not limited to, hospital glassware, hospital working surfaces, restuarant tables, food service working surfaces, bathroom sinks, and anywhere else that it is expected that picornaviruses may be harbored.

Hand contact of nasal mucus may be the most important mode of rhinovirus transmission. Sterilization of the hands of people coming into contact with persons infected with rhinovirus prevents further spread of the disease. It is contemplated that a compound of the invention incorporated into a hand washing or hand care procedure or product, inhibits production of rhinovirus and decreases the likelihood of the transmission of the disease.

We claim:

1. A compound of formula;

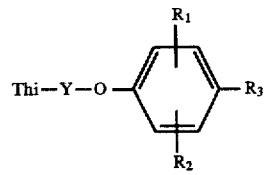

Formula I wherein:

Thi is thiadiazolyl or thiadiazolyl substituted with alkoxy, fluoromethyl, difluoromethyl, trifluoromethyl, 1,1-difluoroethyl, halo, alkyl, cycloalkyl, hydroxyalkyl, or alkoxyalkyl;

Y is an alkylene bridge of 3–9 carbon atoms;

$R_1$ and $R_2$ are each independently chosen from hydrogen, halo, alkyl, alkenyl, amino, alkylthio, hydroxy, hydroxyalkyl, alkoxyalkyl, alkylthioalkyl, alkylsulfinyl alkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl, or cyano;

$R_3$ is heterocycle chosen from pyrimidinyl, pyrazinyl, or pyridazinyl, or a pharmaceutically acceptable salt thereof.

2. A compound according to claim 1 wherein Y is a linear hydrocarbon chain of three to about five carbons.

3. A pharmaceutical composition containing as an active ingredient an antipicornally effective amount of a compound according to claim 1 together with a physiologically acceptable carrier.

4. A method of treating picornaviral infection in a mammalian host comprising administering an antipicornavirally effective amount of a compound according to claim 1.

5. A method of combating picornaviruses comprising contacting the locus of said viruses with a compound of claim 1.

* * * * *